US012760252B2

(12) United States Patent
Hsu et al.

(10) Patent No.: US 12,760,252 B2
(45) **Date of Patent: *Oct. 13, 2026**

(54) BIOLOGICAL TISSUE FORMING METHOD, BIOLOGICAL TISSUE FORMING PACKAGE AND BIOLOGICAL TISSUE DISPENSING SYSTEM

(71) Applicant: INDUSTRIAL TECHNOLOGY RESEARCH INSTITUTE, Hsinchu (TW)

(72) Inventors: Chao-Hong Hsu, Tainan City (TW); Teng-Yen Wang, Yunlin County (TW); Yang-Cheng Lin, Chiayi City (TW); Hsin-Yi Hsu, Taoyuan City (TW); Yu-Bing Liou, Hsinchu City (TW); Chang-Chou Li, Tainan City (TW); Chih-Hung Huang, Tainan City (TW); Tung-Ying Lin, Kaohsiung City (TW); Li-Hsin Lin, Hsinchu County (TW); Yuchi Wang, New Taipei City (TW); Hsin-Hsin Shen, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 447 days.

This patent is subject to a terminal disclaimer.

(21) Appl. No.: 18/542,398

(22) Filed: Dec. 15, 2023

(65) Prior Publication Data

US 2025/0129316 A1 Apr. 24, 2025

(30) Foreign Application Priority Data

Oct. 20, 2023 (TW) ................................ 112140188

(51) Int. Cl.
*C12M 3/00* (2006.01)
*B01L 3/00* (2006.01)
(Continued)

(52) U.S. Cl.
CPC ............ *C12M 21/08* (2013.01); *C12M 23/38* (2013.01); *C12M 25/02* (2013.01); *C12M 29/00* (2013.01); *C12M 31/10* (2013.01)

(58) Field of Classification Search
CPC .............................. C12M 21/08; C12M 25/02
See application file for complete search history.

(56) References Cited

U.S. PATENT DOCUMENTS 8,178,056 B2 * 5/2012 Yokoyama ........ B01L 3/502715 422/402
9,107,979 B2 8/2015 Lin et al.
(Continued)

FOREIGN PATENT DOCUMENTS

CN 214029979 U 8/2021
CN 114292743 A 4/2022
(Continued)

OTHER PUBLICATIONS

TW Notice of Allowance Dated Jun. 3, 2024 as received in Application No. 112140188.
(Continued)

*Primary Examiner* — Nathan A Bowers
(74) *Attorney, Agent, or Firm* — Maschoff Brennan

(57) ABSTRACT

This disclosure relates to a biological tissue forming method includes the following steps: providing a biological tissue forming package with a base, a membrane, a sliding assembly and a sealing film that seals a chamber of the base used for receiving the membrane and the sliding assembly with one of the base and the sealing film being light-transmitting; passing a biological tissue fluid through the sealing film and
(Continued)

the sliding assembly so as to be dispensed on the membrane; moving the sliding assembly away from a covering position used for covering the membrane via at least one passive magnetic element so as to expose the biological tissue fluid on the membrane; and irradiating the biological tissue fluid exposed on the membrane by a curing light transmitting through the one of the base and the sealing film so as to cure the biological tissue fluid into a biological tissue.

13 Claims, 15 Drawing Sheets

(51) Int. Cl.

| | |
|---|---|
| ***C12M 1/00*** | (2006.01) |
| ***C12M 1/12*** | (2006.01) |

(56) References Cited

U.S. PATENT DOCUMENTS

| | | | |
|---|---|---|---|
| 12,258,546 | B2 * | 3/2025 | Hsu ........................ C12M 29/06 |
| 2008/0149840 | A1 * | 6/2008 | Handique ......... B01L 3/502723 250/366 |
| 2018/0087022 | A1 | 3/2018 | Takahashi et al. |
| 2020/0375543 | A1 * | 12/2020 | Chen .................... A61B 5/1455 |
| 2021/0318341 | A1 * | 10/2021 | Oei ......................... B01L 3/508 |
| 2022/0290092 | A9 | 9/2022 | Jovanovich et al. |
| 2023/0026520 | A1 | 1/2023 | Schutte et al. |
| 2023/0114908 | A1 * | 4/2023 | Holenstein .............. A61L 27/52 424/423 |
| 2023/0212491 | A1 | 7/2023 | Wrzesinski et al. |

FOREIGN PATENT DOCUMENTS

| | | | |
|---|---|---|---|
| CN | 113456188 | B | 11/2022 |
| CN | 115777680 | A | 3/2023 |
| CN | 115850729 | A | 3/2023 |
| CN | 116134123 | A | 5/2023 |
| JP | 2001299326 | A | 10/2001 |
| JP | 2018027029 | A | 2/2018 |
| JP | 2021112170 | A | 8/2021 |
| TW | 202033762 | A | 9/2020 |
| TW | I753622 | B | 1/2022 |
| TW | I796893 | B | 3/2023 |
| TW | 202325829 | A | 7/2023 |
| WO | 2021/119486 | A1 | 6/2021 |

OTHER PUBLICATIONS

JP Office Action mailed on Aug. 19, 2025 for application 2024097804.
Tetsutaro Kikuchi et al., "A novel, flexible and automated manufacturing facility for cell-based health care products: Tissue Factory," The Japanese Society for Regenerative Medicine. 2018.
JP Notice of Allowance Dated Jan. 27, 2026 as received in Application No. 2024-097804.
JP Office Action Dated Jan. 27, 2026 as received in Application No. 2024-097804.
Kikuchi, Tetsutaro et al., "A novel,flexible and automated manufacturing facility for cell-basedhealth care products: Tissue Factory", Regenerative Therapy, vol. No. 9, Dec. 2018.
Sekine, Hidekazu et al., "Cell Sheet Tissue Engineering for Heart Failure", Etiology and Morphogenesis of Congenital Heart Disease, Jun. 25, 2016.
Koch, Lothar et al. "Skin Tissue Generation by Laser Cell Printing", Biotechnology and Bioengineering, Feb. 13, 2012.

* cited by examiner

50

50

BIOLOGICAL TISSUE FORMING METHOD, BIOLOGICAL TISSUE FORMING PACKAGE AND BIOLOGICAL TISSUE DISPENSING SYSTEM

CROSS-REFERENCE TO RELATED APPLICATIONS

This non-provisional application claims priority under 35 U.S.C. § 119(a) on Patent Application No(s). 112140188 filed in Taiwan, R.O.C. on Oct. 20, 2023, the entire contents of which are hereby incorporated by reference.

TECHNICAL FIELD

The present disclosure relates to a biological tissue forming method, a biological tissue forming package and a biological tissue dispensing system, more particularly to a method using a biological tissue forming package and a biological tissue dispensing system for forming biological tissue.

BACKGROUND

Cell sheets can cover wounds to improve the healing speed of the wounds and thus are widely used in the biomedical field.

Currently, cell sheets are generally formed by culturing the collected cells in a culture center for a long time, and then the formed cell sheets are transported to various medical facilities for future usage as a clinical application through a transportation environment with appropriate control factors such as temperature or humidity.

However, cell sheets currently need to be formed in a specific culture center, which is time-and-cost-consuming. Moreover, a risk such as contamination or damage of the cell sheets may be occurred during the transportation or the preservation for future usage of the cell sheets. Therefore, how to develop a method, a component or a system for quickly and low-costly forming cell sheets near the clinical site has become an important issue in the related field.

SUMMARY

The present disclosure provides a biological tissue forming method, a biological tissue forming package and a biological tissue dispensing system.

According to one aspect of the present disclosure, a biological tissue forming method includes the following steps: providing a biological tissue forming package, wherein the biological tissue forming package includes a base, a membrane, a sliding assembly and a sealing film, the base has a chamber for receiving the membrane and the sliding assembly, the sliding assembly is located at a covering position to cover the membrane, the sealing film seals the chamber, and one of the base and the sealing film is light-transmitting; passing a biological tissue fluid through the sealing film and the sliding assembly so as to be dispensed on the membrane; moving the sliding assembly away from the covering position via at least one passive magnetic element so as to expose the biological tissue fluid on the membrane; and irradiating the biological tissue fluid exposed on the membrane by a curing light transmitting through the one of the base and the sealing film so as to cure the biological tissue fluid into a biological tissue.

According to another aspect of the present disclosure, a biological tissue forming package includes a base, a membrane, a sliding assembly, at least one passive magnetic element, and a sealing film. The base has a chamber and a supporting surface located in the chamber. The membrane is made of a hydrophilic material, and the membrane is disposed on the supporting surface of the base. The sliding assembly is movably disposed in the chamber of the base between a covering position and an exposing position. When the sliding assembly is located at the covering position, the sliding assembly correspondingly covers the membrane. When the sliding assembly is located at the exposing position, the sliding assembly is located away from and exposes the membrane. The at least one passive magnetic element is attached to the sliding assembly, and the at least one passive magnetic element is configured to be magnetically attracted to move the sliding assembly. The sealing film is disposed on and covers the base to seal the chamber as well as the membrane, the sliding assembly and the at least one passive magnetic element inside the chamber. One of the base and the sealing film is light-transmitting. When the sliding assembly is located at the covering position, the sealing film and the sliding assembly are configured for a biological tissue fluid to pass therethrough so as to dispense the biological tissue fluid on the membrane. When the sliding assembly is located at the exposing position, the one of the base and the sealing film is configured for a curing light to transmitting therethrough so as to irradiate the biological tissue fluid exposed on the membrane and cure the biological tissue fluid into a biological tissue.

According to further another aspect of the present disclosure, a biological tissue dispensing system adapted for the abovementioned biological tissue forming package includes a carrier, at least one active magnetic element, and a dispenser. The carrier includes a carrier body and a lid. The carrier body has an accommodation space that is configured to accommodate the biological tissue forming package. The lid is coupled to the carrier body for selectively opening or closing the accommodation space, and the lid has a dispensing hole in communication with the accommodation space. The at least one active magnetic element is movably attached to the lid. When the lid closes the accommodation space, the at least one active magnetic element is configured to magnetically attract the at least one passive magnetic element of the biological tissue forming package so as to move the sliding assembly between the covering position and the exposing position. The dispenser is movably mounted with respect to the carrier, and the dispenser is configured to receive the biological tissue fluid therein. When the lid closes the accommodation space, one end of the dispenser is configured to move and pass through the dispensing hole, the sealing film and the sliding assembly so as to dispense the biological tissue fluid on the membrane.

BRIEF DESCRIPTION OF THE DRAWINGS

The present disclosure will become more fully understood from the detailed description given hereinbelow and the accompanying drawings which are given by way of illustration only and thus are not intending to limit the present disclosure and wherein.

DETAILED DESCRIPTION

Aspects and advantages of the invention will become apparent from the following detailed descriptions with the accompanying drawings. For purposes of explanation, one or more specific embodiments are given to provide a thorough understanding of the invention, and which are described in sufficient detail to enable one skilled in the art to practice the described embodiments. It should be understood that the following descriptions are not intended to limit the embodiments to one specific embodiment. On the contrary, it is intended to cover alternatives, modifications, and equivalents as can be included within the spirit and scope of the described embodiments as defined by the appended claims.

Figure 1:
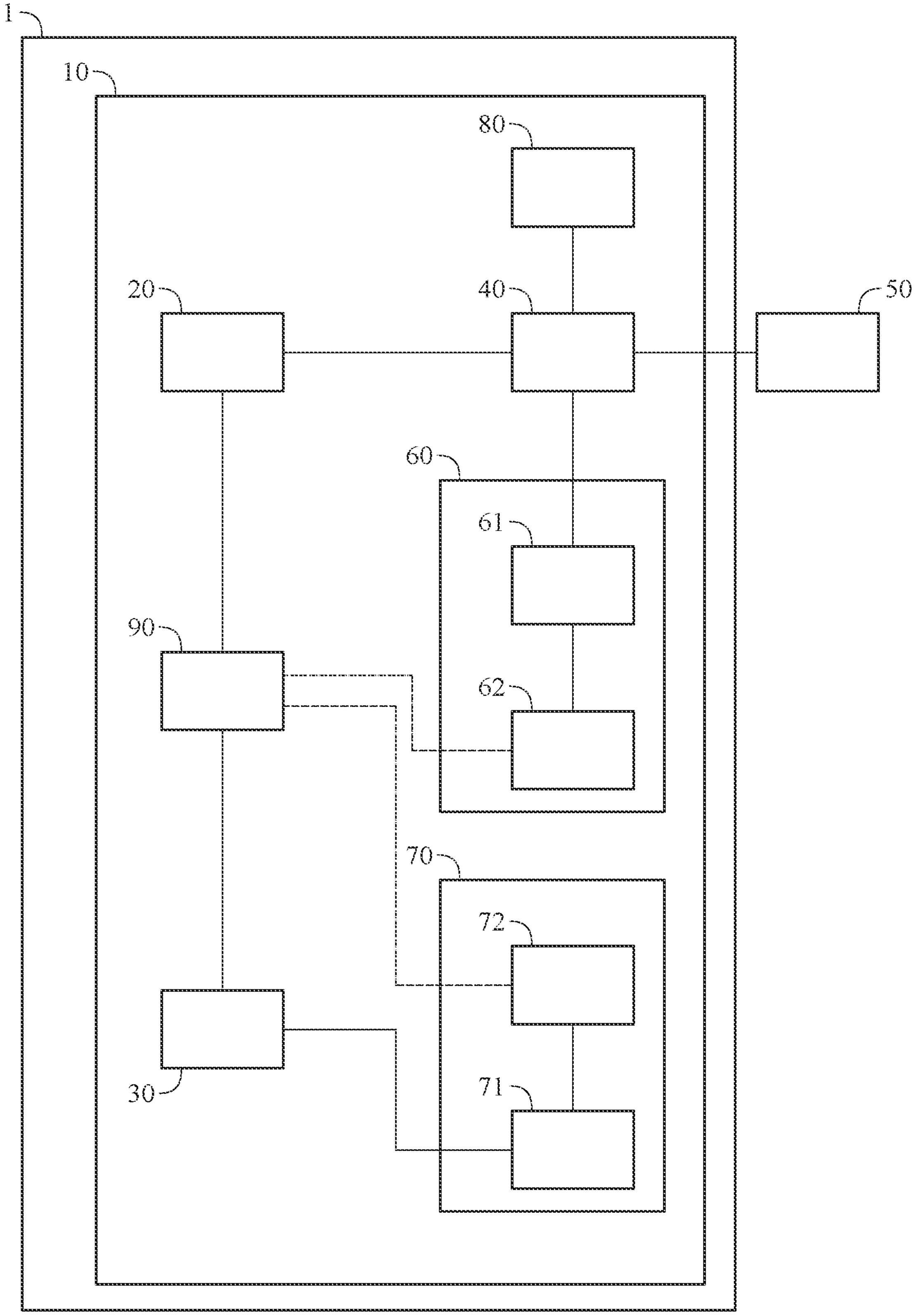
FIG. 1 is a block diagram of a biological tissue dispensing system according to one embodiment of the present disclosure.
Figure 2:
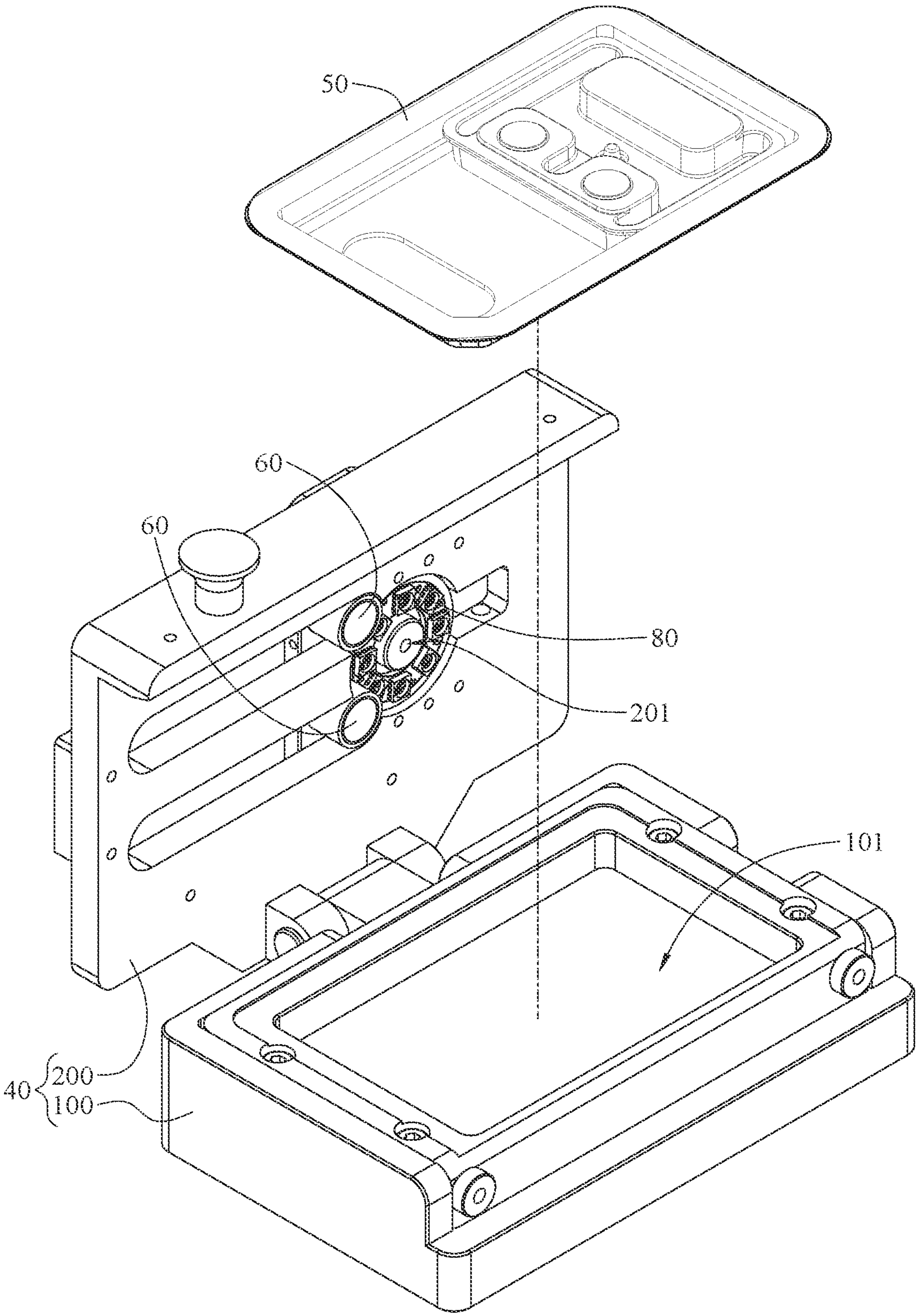
FIG. 2 is an exploded view of several parts of the biological tissue dispensing system of FIG. 1.
Figure 3:
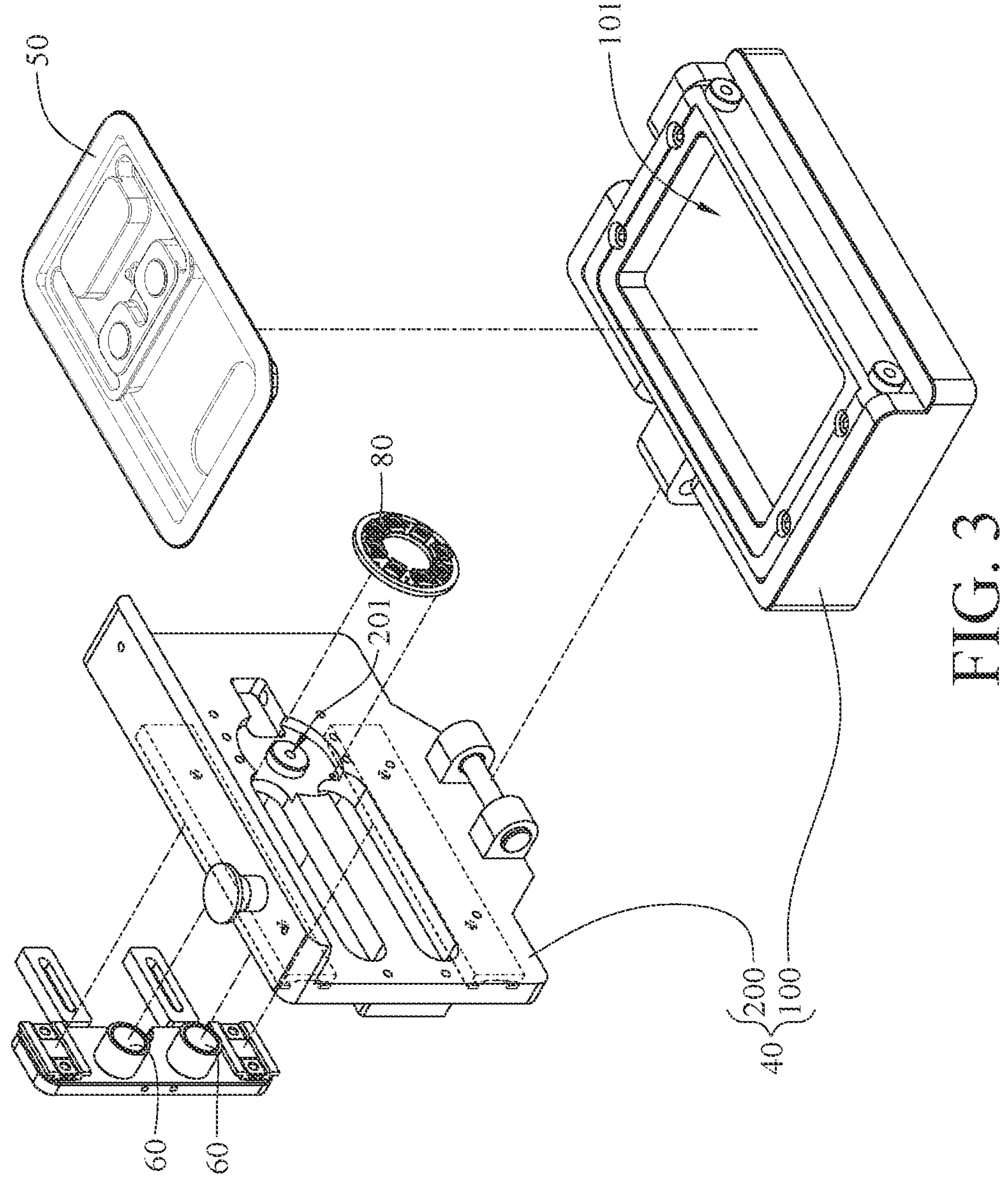
FIG. 3 is another exploded view of the several parts of the biological tissue dispensing system of FIG. 2.

Please refer to FIG. 1 to FIG. 3, where FIG. 1 is a block diagram of a biological tissue dispensing system according to one embodiment of the present disclosure, FIG. 2 is an exploded view of several parts of the biological tissue dispensing system of FIG. 1, and FIG. 3 is another exploded view of the several parts of the biological tissue dispensing system of FIG. 2.

A biological tissue dispensing system 1 provided in one embodiment of the present disclosure may include a forming machine 10, a first drive mechanism 20, a second drive mechanism 30, a carrier 40, an active magnetic module 60, a dispensing module 70, a light source 80 and a controller 90.

The forming machine 10 receives the first drive mechanism 20, the second drive mechanism 30, the carrier 40, the active magnetic module 60, the dispensing module 70 and the light source 80 therein. In one embodiment, the forming machine 10, for example, has a gate (not shown) which can be opened or closed, such that a biological tissue forming package 50 may be placed into the forming machine 10 when the gate is opened, and the forming machine 10 can isolate external light from emitting therein when the gate is closed. Specifically, the gate of the forming machine 10 can be closed when the biological tissue dispensing system 1 is operating, and there is only light emitted from the light source 80 inside the forming machine 10.

The first drive mechanism 20 may be, for example, an electric cylinder with a motor assembly that can be horizontally placed. The second drive mechanism 30 may be, for example, an electric cylinder with a motor assembly that can be vertically disposed. Each of the first drive mechanism 20 and the second drive mechanism 30 can be in signal communication with the controller 90, and the controller 90 can send a signal to control the movement of the first drive mechanism 20 and the second drive mechanism 30. Please be noted that the formations and the arrangement directions of the first drive mechanism 20 and the second drive mechanism 30 are not intended to restrict the present disclosure. In some other embodiments of the present disclosure, each of the first drive mechanism and the second drive mechanism may be a controllable and movable mechanism, such as a pneumatic cylinder or a hydraulic cylinder. In some other embodiments of the present disclosure, each of the first drive mechanism and the second drive mechanism may be disposed in an arbitrary direction.

The carrier 40 may be disposed on the first drive mechanism 20 and can be moved by the first drive mechanism 20 along, for example, a horizontal direction. The carrier 40 includes a carrier body 100 and a lid 200. The carrier body 100 has an accommodation space 101. The lid 200 is pivotably coupled to and covers the carrier body 100 and thus can selectively open or close the accommodation space 101. The lid 200 has a dispensing hole 201. The dispensing hole 201 may have a size gradually reduced along a direction towards the carrier body 100 and thus may be, for example, a funnel shape. The dispensing hole 201 is in communication with the accommodation space 101 when the lid 200 covers the carrier body 100. Please be noted that the first drive mechanism 20 is optional. In some other embodiments of the present disclosure, the carrier may be moved by other suitable manner instead of the first drive mechanism. Moreover, in some other embodiments of the present disclosure, the lid may be slidably coupled to the carrier body, and the present disclosure is not limited thereto.

The biological tissue forming package 50 is disposed in the accommodation space 101 of the carrier 40 and can be moved together with the carrier 40 along, for example, a vertical direction. Specifically, the controller 90 can control the first drive mechanism 20 to move the carrier 40 to the position close to the gate of the forming machine 10 when the gate is opened, so that the lid 200 of the carrier 40 can be conveniently opened for placing the biological tissue forming package 50 into the accommodation space 101 of the carrier 40. Then, the controller 90 can control the first drive mechanism 20 to move the carrier 40 and the biological tissue forming package 50 inside the forming machine 10 after the lid 200 is closed.

The active magnetic module 60 includes two active magnetic elements 61 and a third drive mechanism 62. The active magnetic elements 61 may be, for example, permanent magnets movably attached to the lid 200. Please be noted that the quantity of the active magnetic elements 61 is not intended to restrict the present disclosure. In some other embodiments of the present disclosure, active magnetic elements with different quantities may also be arranged depending on actual design requirements, and the present disclosure is not limited thereto. The third drive mechanism 62 is connected to the active magnetic elements 61 and is in signal communication with the controller 90, and the controller 90 can send a signal to control the movement of the third drive mechanism 62.

The dispensing module 70 includes a dispenser 71 and a fourth drive mechanism 72. The dispenser 71 may be, for example, a syringe, but the present disclosure is not limited thereto. The dispenser 71 can be used for accommodating biological tissue fluid. Please be noted that a light curing ingredient for assisting in curing the biological tissue fluid (e.g., photoinitiator in one embodiment) and a cell vector for assisting in carrying the biological tissue fluid (e.g., collagen in one embodiment) can be mixed in the dispenser 71, wherein the percentage proportion of the light curing ingredient may be, for example, 99%, and the percentage proportion of the cell vector may be, for example, 1%. However, the present disclosure is not limited thereto. The fourth drive mechanism 72 is connected to one end of the dispenser 71 (e.g., a piston rod of the syringe) and can be in signal communication with the controller 90, and the controller 90 can send a signal to control the injection amount of the biological tissue fluid from the other end of the dispenser 71 (e.g., a needle of the syringe) through the fourth drive mechanism 72. The dispensing module 70 can be disposed on the second drive mechanism 30 and can be moved towards or away from the carrier 40 by the second drive mechanism 30 along, for example, a vertical direction.

The light source 80 may include a plurality of light-emitting elements (not numbered), and the light source 80 is attached inside the forming machine 10 to provide curing light. In one embodiment, the light source 80 can be attached to the lid 200 of the carrier 40, and the light source 80 can correspond to a supporting surface 302 (shown in FIG. 4) of the biological tissue forming package 50 after the biological tissue forming package 50 is placed into the carrier 40 and the lid 200 is closed.

Figure 4:
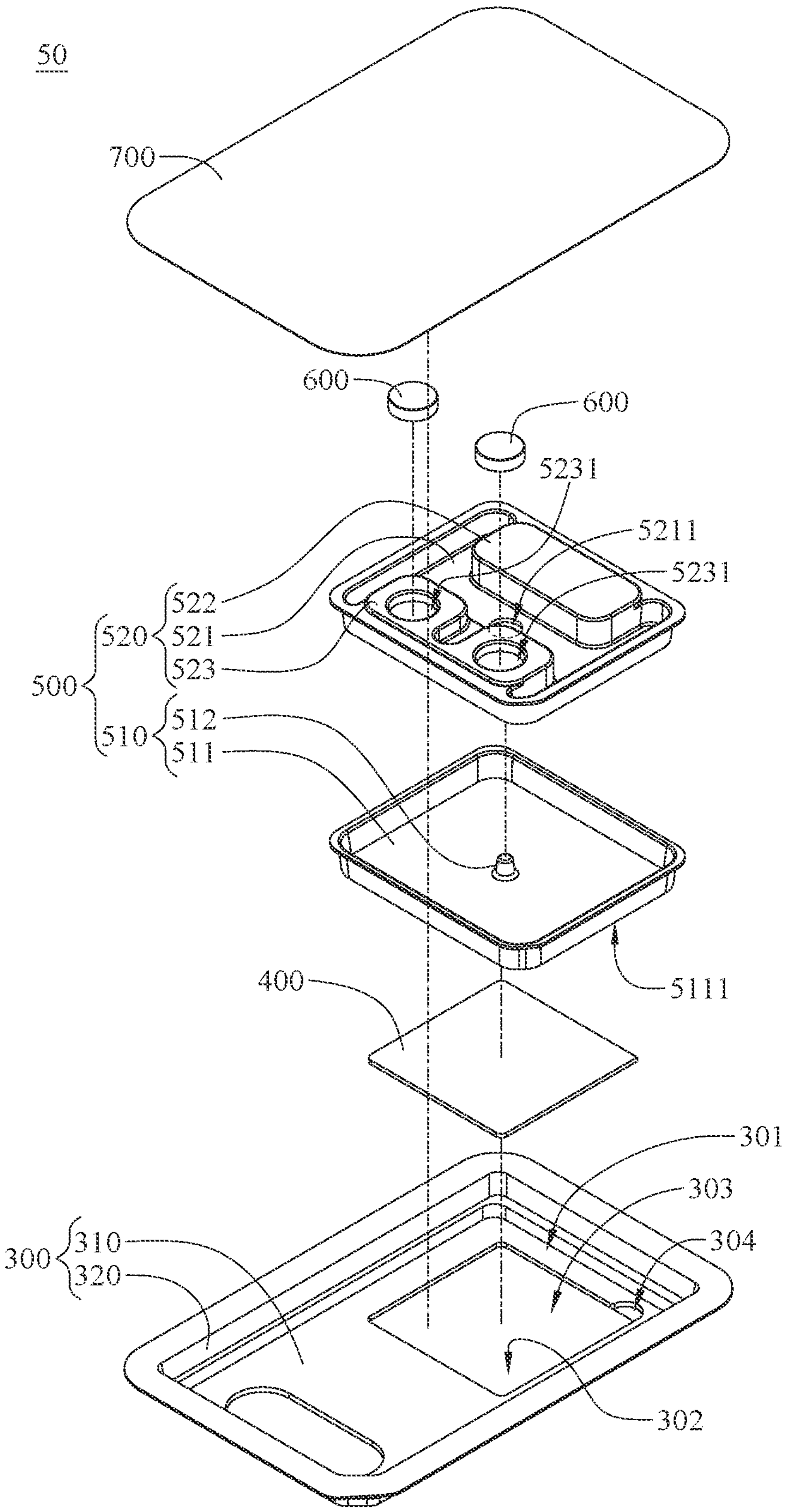
FIG. 4 is an exploded view of a biological tissue forming package of the biological tissue dispensing system of FIG. 2.
Figure 5:
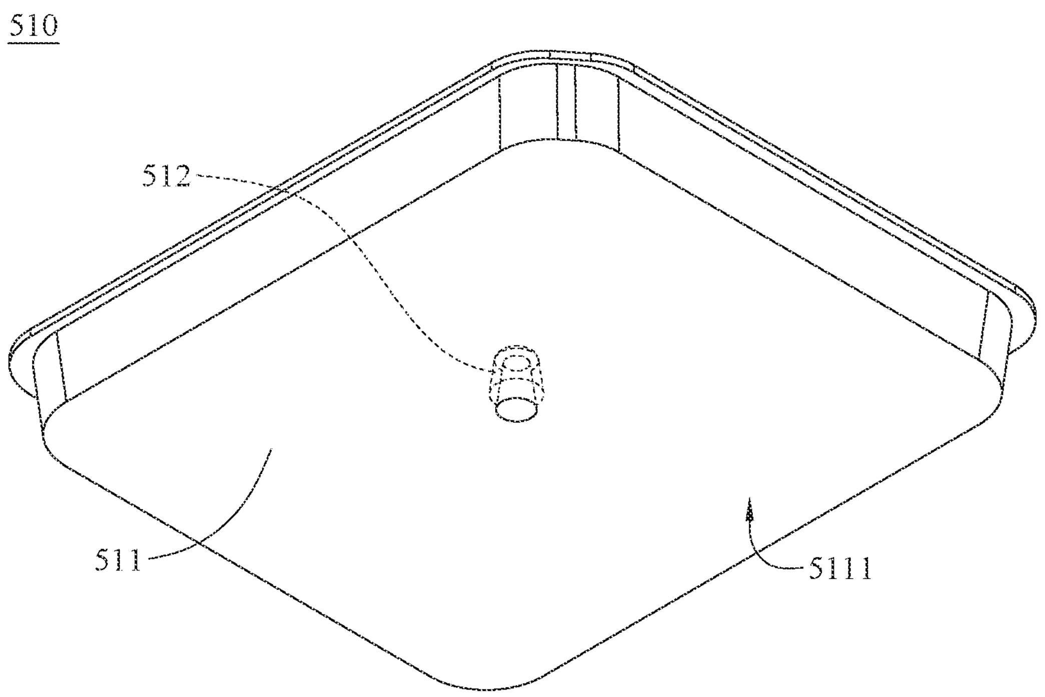
FIG. 5 is a perspective view of a first component of the biological tissue forming package of FIG. 4.

In the following, the biological tissue forming package 50 will be illustrated. Please refer to FIG. 4 to FIG. 5 along with FIG. 2 to FIG. 3, where FIG. 4 is an exploded view of a biological tissue forming package of the biological tissue dispensing system of FIG. 2, and FIG. 5 is a perspective view of a first component of the biological tissue forming package of FIG. 4.

The biological tissue forming package 50 includes a base 300, a membrane 400, a sliding assembly 500, two passive magnetic elements 600 and a sealing film 700.

The base 300 is disposed in the accommodation space 101 of the carrier 40. The base 300 may include a plate 310 and a surrounding lateral wall 320 and may have a chamber 301, a supporting surface 302, a first recess 303 and a second recess 304. The surrounding lateral wall 320 stands on the periphery of the plate 310. The surrounding lateral wall 320 and the plate 310 define the chamber 301. The supporting surface 302 is located in the chamber 301. The supporting surface 302 is recessed from the plate 310 to form the first recess 303. The first recess 303 is in communication with the chamber 301 and corresponds to the dispensing hole 201. The second recess 304 is in communication with the chamber 301 and the first recess 303 for convenient placement or removal of the membrane 400 into or from the first recess 303.

The membrane 400 is made of a hydrophilic material, such as polylactic acid (PLA), or plasma-surface-treated and modified material polycaprolactone (PCL) or collagen, but the present disclosure is not limited thereto. The membrane 400 is disposed on the supporting surface 302 of the base 300 and thus located in the first recess 303. The membrane 400 is configured for biological tissue fluid inside the dispenser 71 to be dispensed thereon.

The sliding assembly 500 may be, for example, a blister pack made of polyethylene terephthalate (PET). The sliding assembly 500 is movable between a covering position and an exposing position in the chamber 301 of the base 300 to cover or expose the membrane 400 through, for example, grooves (not numbered) provided on the surrounding lateral wall 320, wherein the movement direction of the sliding assembly 500 may be the same as the movement direction of the active magnetic elements 61. When the sliding assembly 500 is located at the covering position, the sliding assembly 500 correspondingly covers the membrane 400. When the sliding assembly 500 is located at the exposing position, the sliding assembly 500 is located away from and exposes the membrane 400. Please be noted that the PET material of the sliding assembly 500 is not intended to restrict the present disclosure. In some other embodiments of the present disclosure, the sliding assembly may be a blister pack made of polypropylene (PP), polystyrene (PS) or high density polyethylene (HDPE). In addition, the base 300 may also be a blister pack made of the same material of the sliding assembly 500 for conveniently being made in the same process, but the present disclosure is not limited thereto.

Specifically, the sliding assembly 500 may include a first component 510 and a second component 520. The first component 510 may include a first main body 511 and a positioning element 512. The first main body 511 may have a flat surface 5111, as shown in FIG. 5. The flat surface 5111 faces towards the supporting surface 302. The positioning element 512 and the flat surface 5111 are respectively located at two opposite sides of the first component 510. The positioning element 512 corresponds to the membrane 400 when the sliding assembly 500 covers and is disposed on the first recess 303. The positioning element 512 may be a cylindrical protrusion. The protrusion design is for the dispenser 71 to be aligned with and passed through the positioning element 512. The cylindrical shape design is to provide an escape space for air when dispensing the biological tissue fluid onto the membrane 400, thereby preventing the formation of bubbles in the dispensed biological tissue fluid.

The second component 520 is disposed at a side of the first component 510 having the positioning element 512. The second component 520 may include a second main body 521, a first protrusion 522 and a second protrusion 523. The second main body 521 has an opening 5211 therethrough. The opening 5211 is located between the first protrusion 522 and the second protrusion 523. The opening 5211 can be passed by the positioning element 512 for accomplishing the arrangement of the second component 520 on the first component 510. The first protrusion 522 and the second protrusion 523 are spaced apart from each other on the second main body 521 and are disposed at two opposite sides of the opening 5211 along the movement direction of the sliding assembly 500 (e.g., the direction denoted by the arrow A1 in FIG. 9). Along one dimensional direction, the first protrusion 522 may have a size greater than or equal to a size of the first recess 303 and a size of the membrane 400. The second protrusion 523 has two recesses 5231. In addition, after the arrangement of the biological tissue forming package 50 inside the carrier 40 is accomplished, the positioning element 512 corresponds to the dispensing hole 201 of the carrier 40.

Please be noted that the first component 510 and the second component 520 are two pieces included in the sliding assembly 500, which can reduce forming difficulty and thus save manufacturing costs. However, the present disclosure is not limited thereto. In some other embodiments of the present disclosure, the sliding assembly may be integrally formed.

The passive magnetic elements 600 are respectively accommodated in the recesses 5231 of the second protrusion

523. It can be also considered that the passive magnetic elements 600 are disposed opposite to the first protrusion 522 along the movement direction of the sliding assembly 500 (e.g., the direction denoted by the arrow A1 in FIG. 9). Moreover, the passive magnetic elements 600 can be magnetically attracted to move the sliding assembly 500. Furthermore, after the arrangement of the biological tissue forming package 50 inside the carrier 40 is accomplished, the passive magnetic elements 600 are respectively aligned with the active magnetic elements 61 attached to the carrier 40 so as to be magnetically attracted by the active magnetic elements 61.

The sealing film 700 may be made of, for example, HDPE fiber and thus is light-transmitting. The sealing film 700 can be disposed on the surrounding lateral wall 320 of the base 300 to seal the chamber 301, such that the membrane 400, the sliding assembly 500 as well as the passive magnetic elements 600 are located in the chamber 301 sealed by the sealing film 700. Please be noted that the light-transmitting sealing film 700 that seals the chamber 301 may not be easily noticed in the drawings since the components inside the chamber 301 can still be seen through the sealing film 700. However, the sealing film 700 is in fact existing. Moreover, the first protrusion 522 of the sliding assembly 500 can abut against the sealing film 700 after the sealing film 700 seals the chamber 301, but the present disclosure is not limited thereto. In some other embodiments of the present disclosure, the passive magnetic elements may be magnetically attracted by the active magnetic elements to slightly lift the sliding assembly, so that the first protrusion of the sliding assembly can abut against the sealing film. In addition, in some other embodiments of the present disclosure, the sealing film may be an aluminum foil, a PET film or a PP film, and the present disclosure is not limited thereto.

Figure 6:
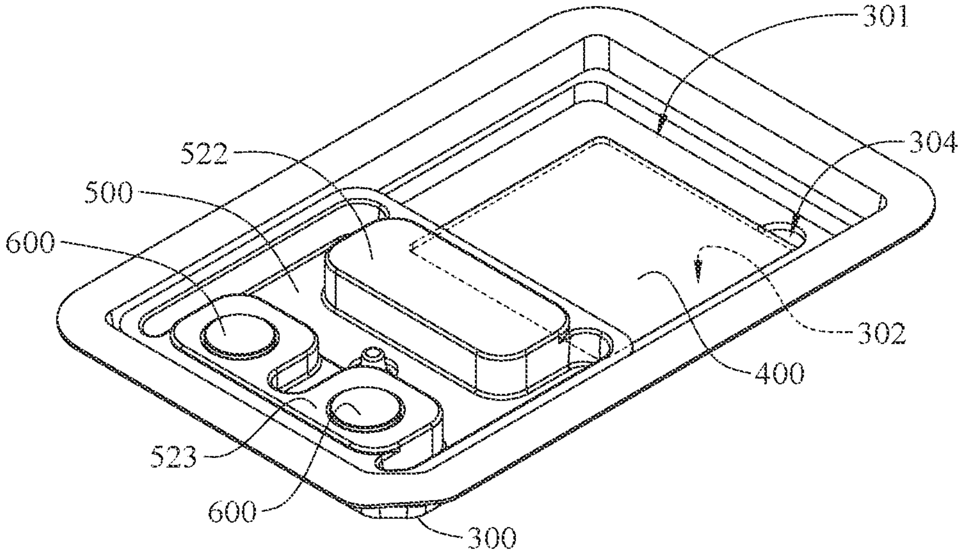
FIG. 6 to FIG. 7 are schematic views showing manufacturing processes of a biological tissue forming package according to one embodiment of the present disclosure.
Figure 7:
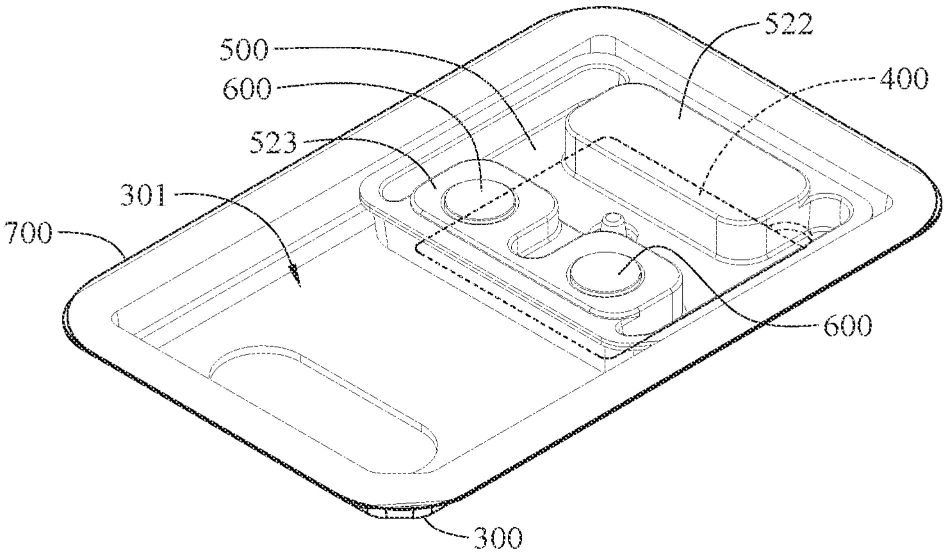
Figure 11:
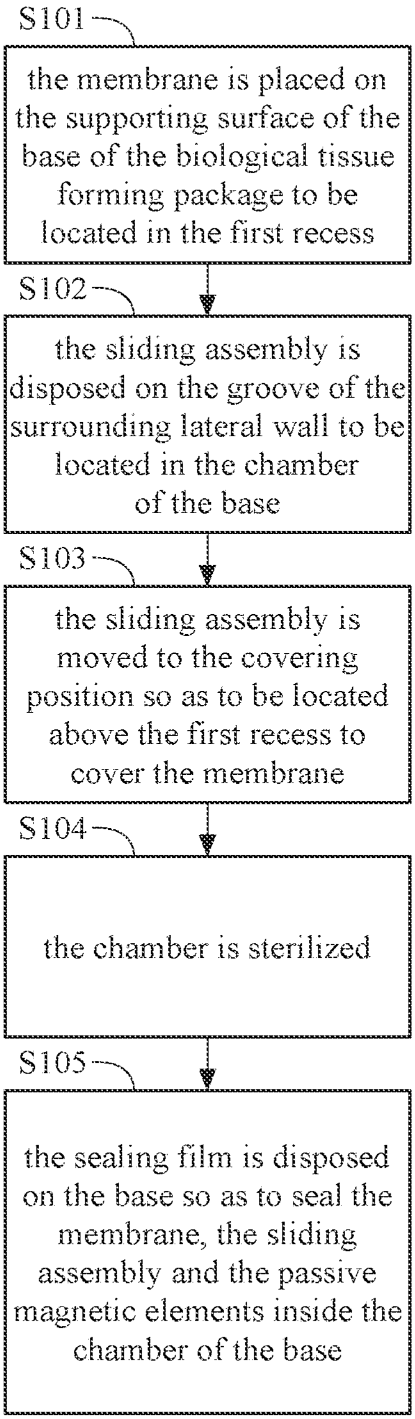
FIG. 11 is a block diagram of the manufacturing processes of the biological tissue forming package of FIG. 6 to FIG. 7.

In the following, manufacturing processes of the biological tissue forming package 50 will be illustrated. Please refer to FIG. 6 to FIG. 7 and FIG. 11 together with FIG. 1 to FIG. 4, where FIG. 6 to FIG. 7 are schematic views showing manufacturing processes of a biological tissue forming package according to one embodiment of the present disclosure, and FIG. 11 is a block diagram of the manufacturing processes of the biological tissue forming package of FIG. 6 to FIG. 7. Please be noted that for clearly showing the working of the biological tissue forming package 50, the carrier 40, the active magnetic module 60 and the light source 80 are omitted in FIG. 6 to FIG. 7.

As shown in FIG. 6, in the step S101, the membrane 400 is placed on the supporting surface 302 of the base 300 of the biological tissue forming package 50 to be located in the first recess 303. Then, in the step S102, the sliding assembly 500 is disposed on the groove of the surrounding lateral wall 320 to be located in the chamber 301 of the base 300.

Then, as shown in FIG. 7, in the step S103, the sliding assembly 500 is moved to the covering position so as to be located above the first recess 303 to cover the membrane 400. The sliding assembly 500 is prevented from falling into the first recess 303 due to its arrangement on the groove of the surrounding lateral wall 320. Meanwhile, the first protrusion 522, corresponds to one side of the membrane 400, as shown in FIG. 7. Then, in the step S104, the chamber 301 is sterilized. Then, in the step S105, the sealing film 700 is disposed on the base 300 so as to seal the membrane 400, the sliding assembly 500 and the passive magnetic elements 600 inside the chamber 301 of the base 300.

So far, the manufacture of the biological tissue forming package 50 is accomplished. The biological tissue forming package 50 can be mass-produced and transported to various medical facilities for future usage. Since biological ingredient, at this moment, is absent from the biological tissue forming package 50, a particular environment provided during transportation or preservation of the biological tissue forming package 50 is not needed, which can reduce the transportation and preservation cost thereof, and any risk such as contamination or damage of biological ingredient will not occur during transportation or preservation. Furthermore, the forming machine 10 is small-sized and reasonably priced and thus can be widely provided in various medical facilities.

Figure 8:
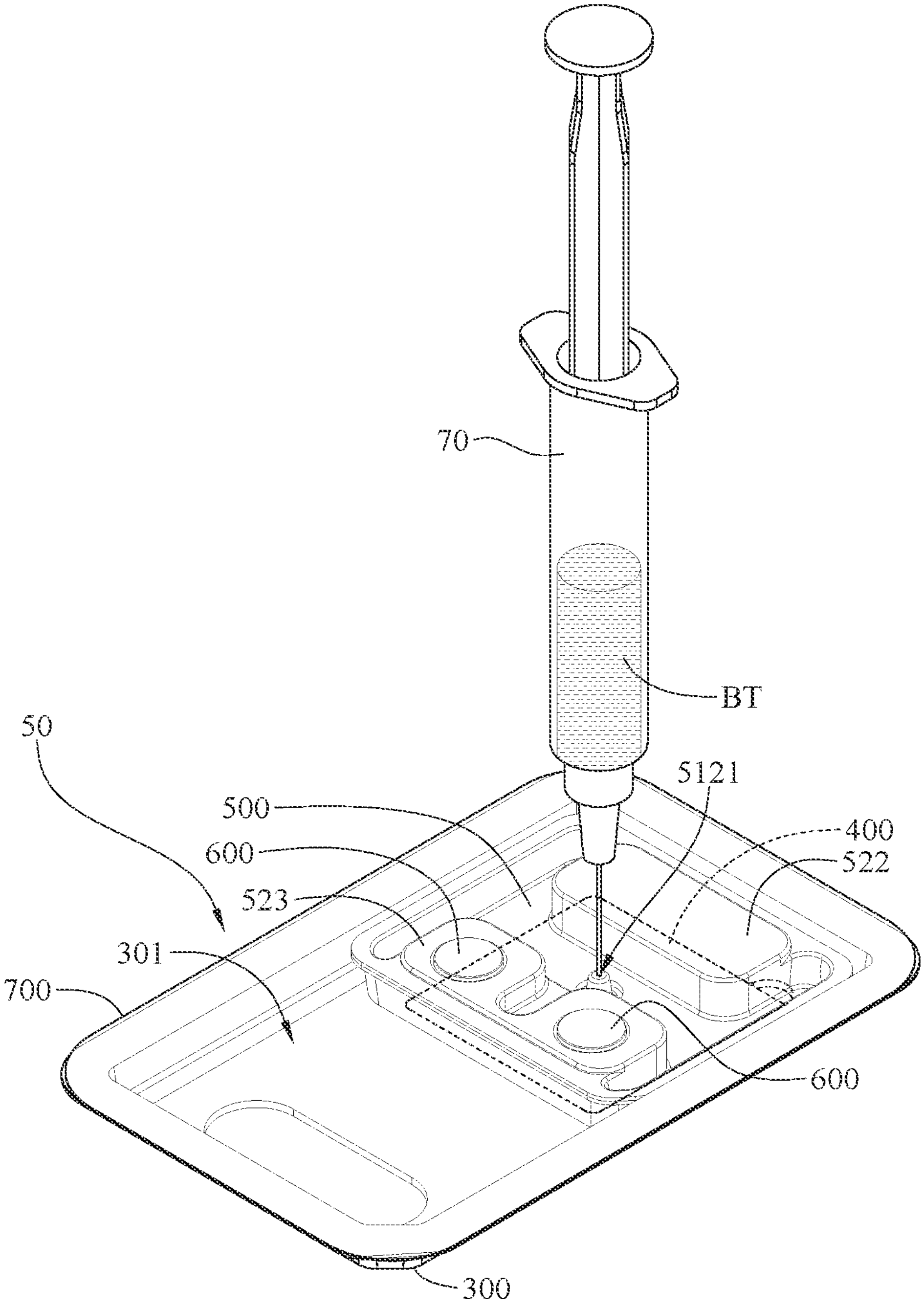
FIG. 8 to FIG. 10 are schematic views showing processes of a biological tissue forming method according to one embodiment of the present disclosure.
Figure 9:
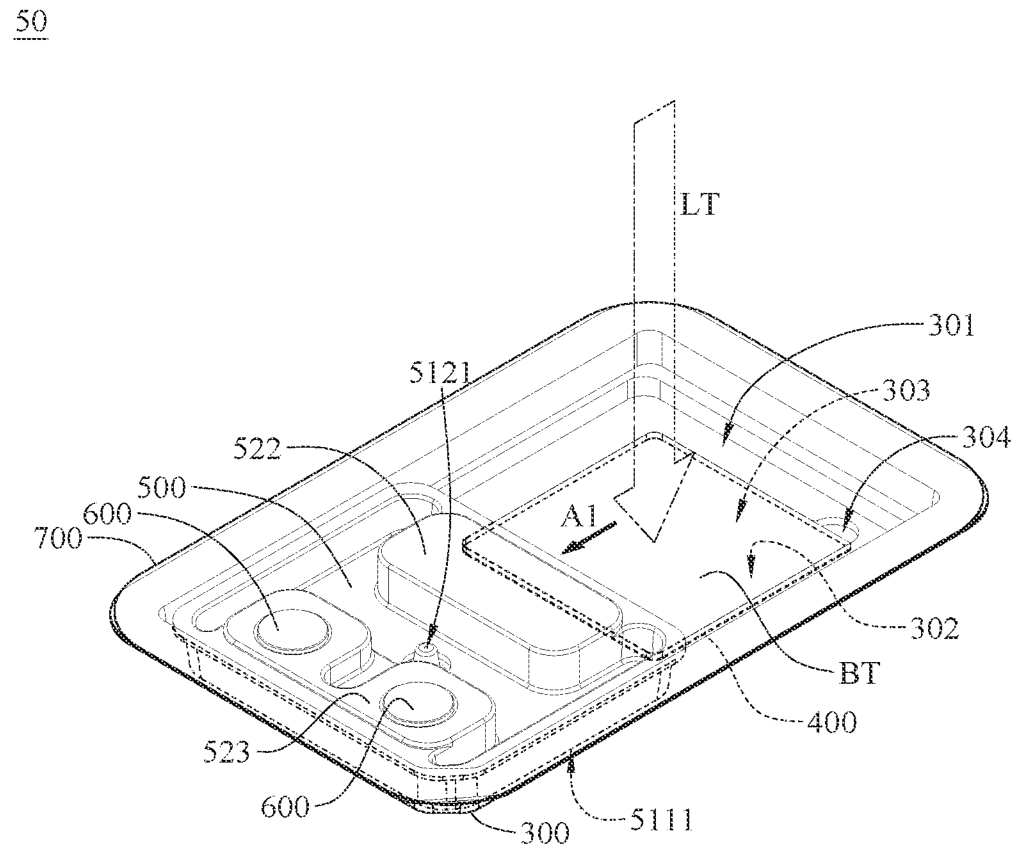
Figure 10:
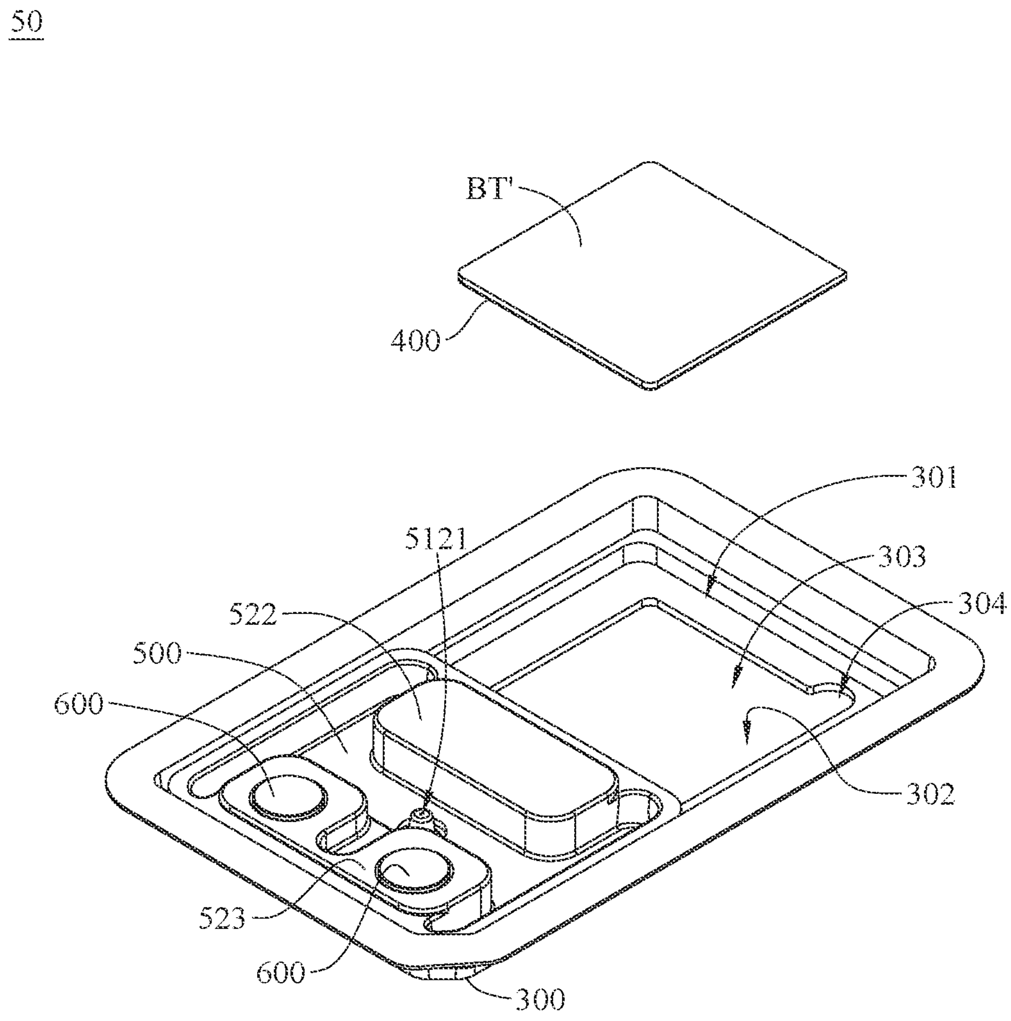
Figure 12:
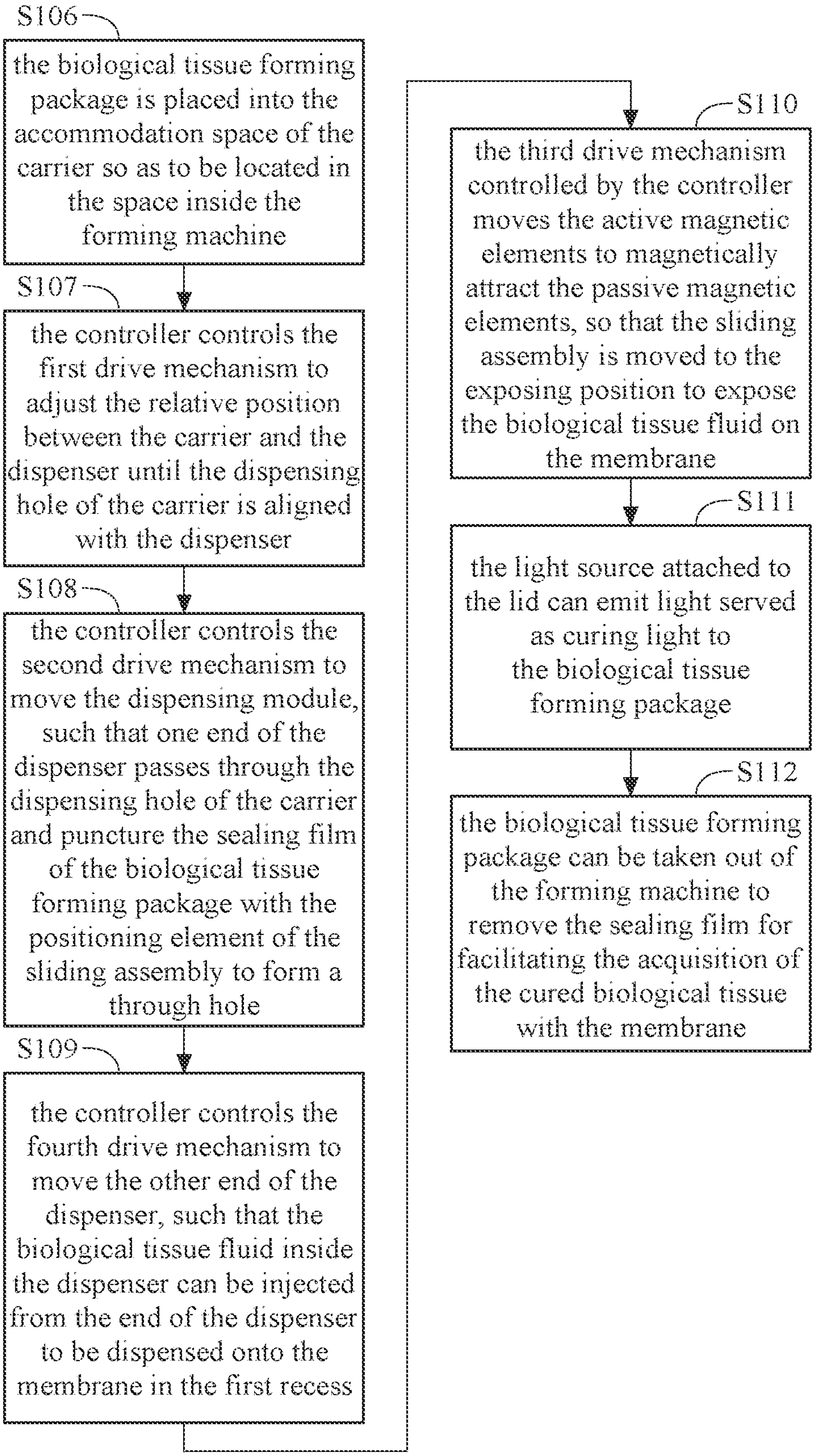
FIG. 12 is a block diagram of the manufacturing processes of the biological tissue forming method of FIG. 8 to FIG. 10.

In the following, the biological tissue forming method achieved by using the biological tissue dispensing system 1 will be illustrated. Please refer to FIGS. 8 to 10 and FIG. 12 together with FIG. 1 to FIG. 4, where FIG. 8 to FIG. 10 are schematic views showing processes of a biological tissue forming method according to one embodiment of the present disclosure, and FIG. 12 is a block diagram of the manufacturing processes of the biological tissue forming method of FIG. 8 to FIG. 10. Please be noted that for clearly showing the working of the biological tissue forming package 50, the carrier 40, the active magnetic module 60 and the light source 80 are omitted in FIG. 8 to FIG. 10.

When the biological tissue forming package 50 transported to a medical facility need to be used in a clinical application, the biological tissue forming package 50 can be placed into the forming machine 10, as abovementioned. Specifically, in the step S106, the biological tissue forming package 50 is placed into the accommodation space 101 of the carrier 40 so as to be located in the space inside the forming machine 10 that is isolated from external light when the gate of the forming machine 10 is closed. Then, in the step S107, the controller 90 controls the first drive mechanism 20 (shown in FIG. 1) to adjust the relative position between the carrier 40 and the dispenser 71 until the dispensing hole 201 of the carrier 40 is aligned with the dispenser 71.

Then, as shown in FIG. 8, in the step S108, the controller 90 controls the second drive mechanism 30 (shown in FIG. 1) to move the dispensing module 70, such that one end of the dispenser 71 (e.g., a needle) passes through the dispensing hole 201 of the carrier 40 (shown in FIG. 2 and FIG. 3) and puncture the sealing film 700 of the biological tissue forming package 50 with the positioning element 512 of the sliding assembly 500 to form a through hole 5121 until the end of the dispenser 71 reaches the chamber 301 thus to be located above the membrane 400. Please be noted that even the dispenser 71 may not be perfectly aligned with the dispensing hole 201 with a slight offset therebetween due to movement or manufacturing tolerance, the funnel shape of the dispensing hole 201 can still guide the end of the dispenser 71 (e.g., a needle) to be easily aligned with and puncture the positioning element 512 when passing through the dispensing hole 201. Then, in the step S109, the controller 90 controls the fourth drive mechanism 72 (shown in FIG. 1) to move the other end of the dispenser 71 (e.g., a piston rod of the syringe), such that the biological tissue fluid BT inside the dispenser 71 can be injected from the end of the dispenser 71 (e.g., the needle of the syringe) to be dispensed onto the membrane 400 in the first recess 303. Since the membrane 400 is made of the hydrophilic material, the biological tissue fluid BT dispensed on the membrane 400 can be quickly spread and thus evenly distributed on the membrane 400. Moreover, the air originally located between the flat surface 5111 and the membrane 400 would enter into the escape space provided by the cylindrical positioning element 512 instead of forming bubbles in the dispensed biological tissue fluid BT after the biological tissue fluid BT is dispensed.

Then, as shown in FIG. 9, in the step S110, the third drive mechanism 62 (shown in FIG. 1) controlled by the controller 90 moves the active magnetic elements 61 (shown in FIG. 2 and FIG. 3) to magnetically attract the passive magnetic elements 600, so that the sliding assembly 500 is moved to the exposing position along the direction denoted by the arrow A1 to expose the biological tissue fluid BT on the membrane 400. Please be noted that the first protrusion 522 is designed to abut against the sealing film 700 after mounted or lifted with the movement of the passive magnetic elements 600, and the first protrusion 522 is able to continuously abut against the sealing film 700 during the movement of the sliding assembly 500 from the covering position to the exposing position. Therefore, even if the sliding assembly 500 is forced at one side, the sliding assembly 500 still remains even under the cooperation of the abutment of the first protrusion 522 against the sealing film 700, thereby ensuring the flat surface 5111 can stay substantially in parallel to the supporting surface 302 during the movement of the sliding assembly 500. Accordingly, the biological tissue fluid BT in the first recess 303 with a specific depth can have a smooth exposed surface contributed by the contact of the substantially parallel flat surface 5111 moved with the sliding assembly 500. Moreover, when the sliding assembly 500 is moved from the covering position (as shown in FIG. 8) to the exposing position (as shown in FIG. 9), the first protrusion 522 can correspond from one side to the opposite side of the membrane 400. Accordingly, the smoothening of the exposed surface of the biological tissue fluid BT contributed by the corresponding area of the flat surface 5111 is ensured during the movement of the first protrusion 522 from the covering position to the exposing position under the cooperation of the abutment of the first protrusion 522 against the sealing film 700. Then, in the step S111, the light source 80 attached to the lid 200 (shown in FIG. 2 and FIG. 3) can emit light served as curing light LT to the biological tissue forming package 50, which passes through the light-transmitting sealing film 700 to irradiate emit the biological tissue fluid BT exposed on the membrane 400 within a predetermined period of time. With the cooperation of the light curing ingredient, the biological tissue fluid BT can be cured into biological tissue BT' (as shown in FIG. 10). In one embodiment of the present disclosure, the abovementioned predetermined period can be, for example, 30 seconds. However, the present disclosure is not limited thereto. In some other embodiments of the present disclosure, the light source emitting the curing light may have different setting conditions to therefore affect the forming time of the biological tissue fluid. Thus, the light source may be configured with a different condition to emit different curing light depending on actual requirements, so that the forming time of the biological tissue fluid can be flexibly adjusted. That is, in some other embodiments of the present disclosure, the predetermined period may be different based on different curing light emitted from a light source with a different setting condition.

The curing light LT for light curing may be visible light, ultraviolet light, or infrared light, and the present disclosure is not limited thereto. Please be noted that the curing light LT referred to in the present disclosure is provided by the light source 80 received inside the forming machine 10 that is isolated from external light, instead of light incident into the forming machine 10. That is, the biological tissue forming method of the present disclosure can be implemented in a space isolated from external light. However, the present disclosure is not limited thereto. In some other embodiments of the present disclosure, the biological tissue forming method of the present disclosure may be implemented in an environment with ambient natural light, such as the inner space of the forming machine with the gate thereof opened or a normal desktop. That is, when the biological tissue forming method is implemented in an environment with ambient natural light, the ambient natural light and the curing light emitted from the light source all irradiate the biological tissue fluid.

The cured biological tissue BT' is adhered onto the membrane 400. Then, as shown in FIG. 10, in the step S112, the biological tissue forming package 50 can be taken out of the forming machine 10 (shown in FIG. 1) to remove the sealing film 700 (shown in FIG. 9) for facilitating the acquisition of the cured biological tissue BT' with the membrane 400 by using a tool such as tweezers (not shown) to move the membrane 400 from the bottom of the first recess 303 via the second recess 304.

Compared to the biological tissue fluid cured by heating in the conventional manner, the present disclosure can provide a stable environment for curing the biological tissue fluid BT in a short time of about 30 seconds. Therefore, the biological tissue BT' can be instantly produced for immediate usage after appropriate cells are collected from the cell bank. There is no need to provide a particular environment to transport or preserve the cured biological tissue BT' for future usage, which can reduce the transportation and preservation cost of the biological tissue BT', and any risk such as contamination or damage to the biological tissue BT' will be minimized during transportation or preservation.

Furthermore, the heating used for curing biological tissue in the conventional manner may damage cells due to improper temperature control. In comparison, using the light source 80 to irradiate the biological tissue fluid BT provides a stable forming environment.

Moreover, with the design of the first recess 303, the cured biological tissue BT' can be easily taken out with the membrane 400, preventing damage of the biological tissue BT' caused by high temperature of laser cutting used for facilitating the acquisition of cured biological tissue BT' in the conventional manner.

Additionally, since the biological tissue fluid BT is cured after being smoothened through the flat surface 5111 of the sliding assembly 500, the exposed surface of the cured and formed biological tissue BT' is flat and thus can be adapted to different kinds of wounds.

Also, since the chamber 301 sealed in the biological tissue forming package 50 is sterilized without biological ingredient therein before dispensing the biological tissue fluid BT, the biological tissue forming package 50 can be low-costly mass-produced and then can be easily and low-costly transported to and preserved at various medical facilities for future usage.

In addition, the sliding assembly 500 can be moved in a contactless manner via the active magnetic elements 61 for maintaining the sterility of the chamber 301 before dispensing the biological tissue fluid BT therein.

Figure 13:
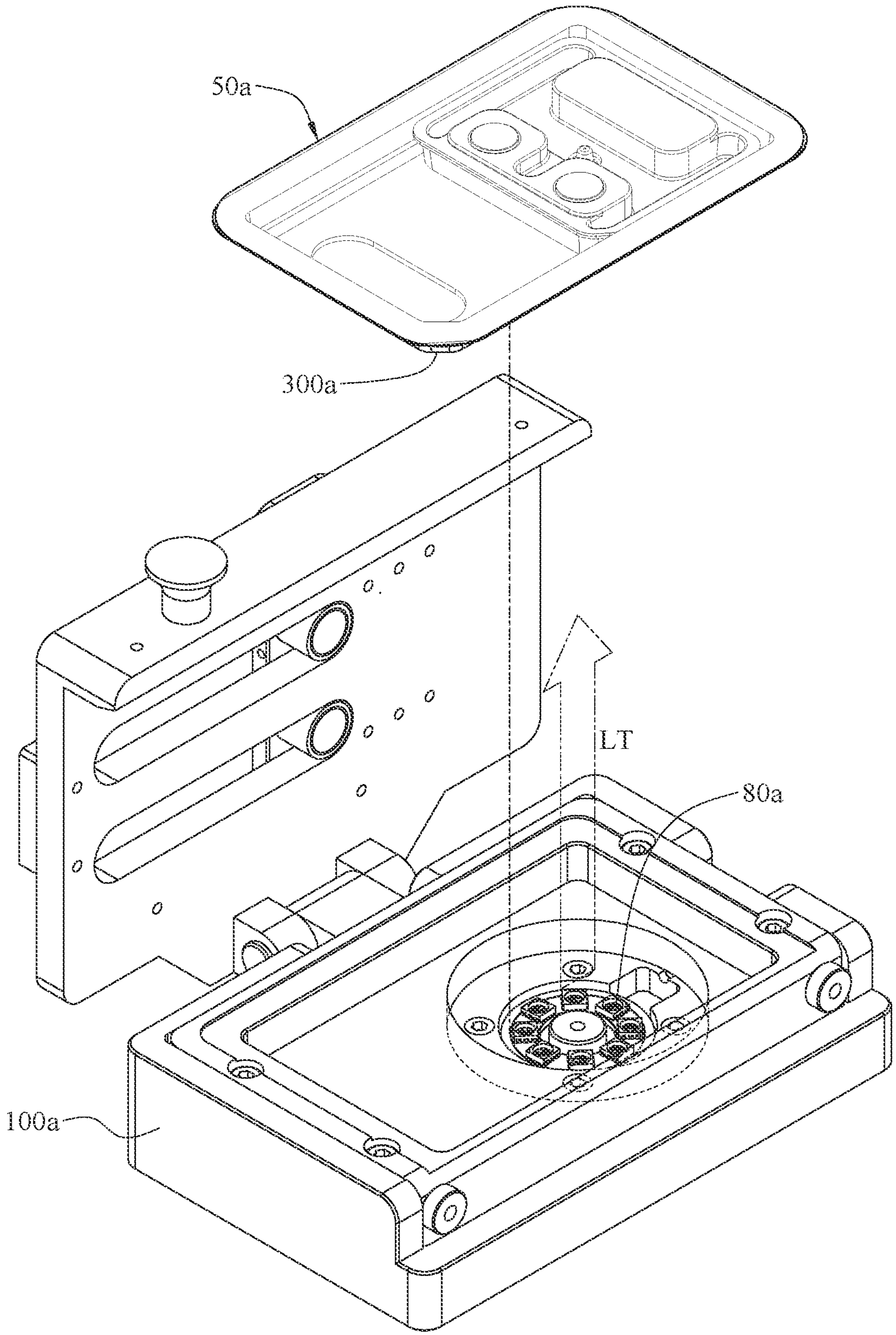
FIG. 13 is an exploded view of several parts of a biological tissue dispensing system according to another embodiment of the present disclosure.

In the one or more abovementioned embodiments, the light source 80 is attached to the lid 200 of the carrier 40, but the present disclosure is not limited thereto. Please refer to FIG. 13, which is an exploded view of several parts of a biological tissue dispensing system according to another embodiment of the present disclosure. Note that only differences between this and abovementioned embodiments will be illustrated hereinafter with the similar description omitted.

In this embodiment, the base 300*a* of the biological tissue forming package 50*a* is light-transmitting. The light source 80*a* is attached to the bottom of the carrier body 100*a* so as to provide curing light LT travelling into the biological tissue forming package 50*a* through the base 300*a* from the bottom of the biological tissue forming package 50*a* for irradiating the biological tissue fluid therein, and the biological tissue fluid irradiated from the bottom can also be cured.

Figure 14:
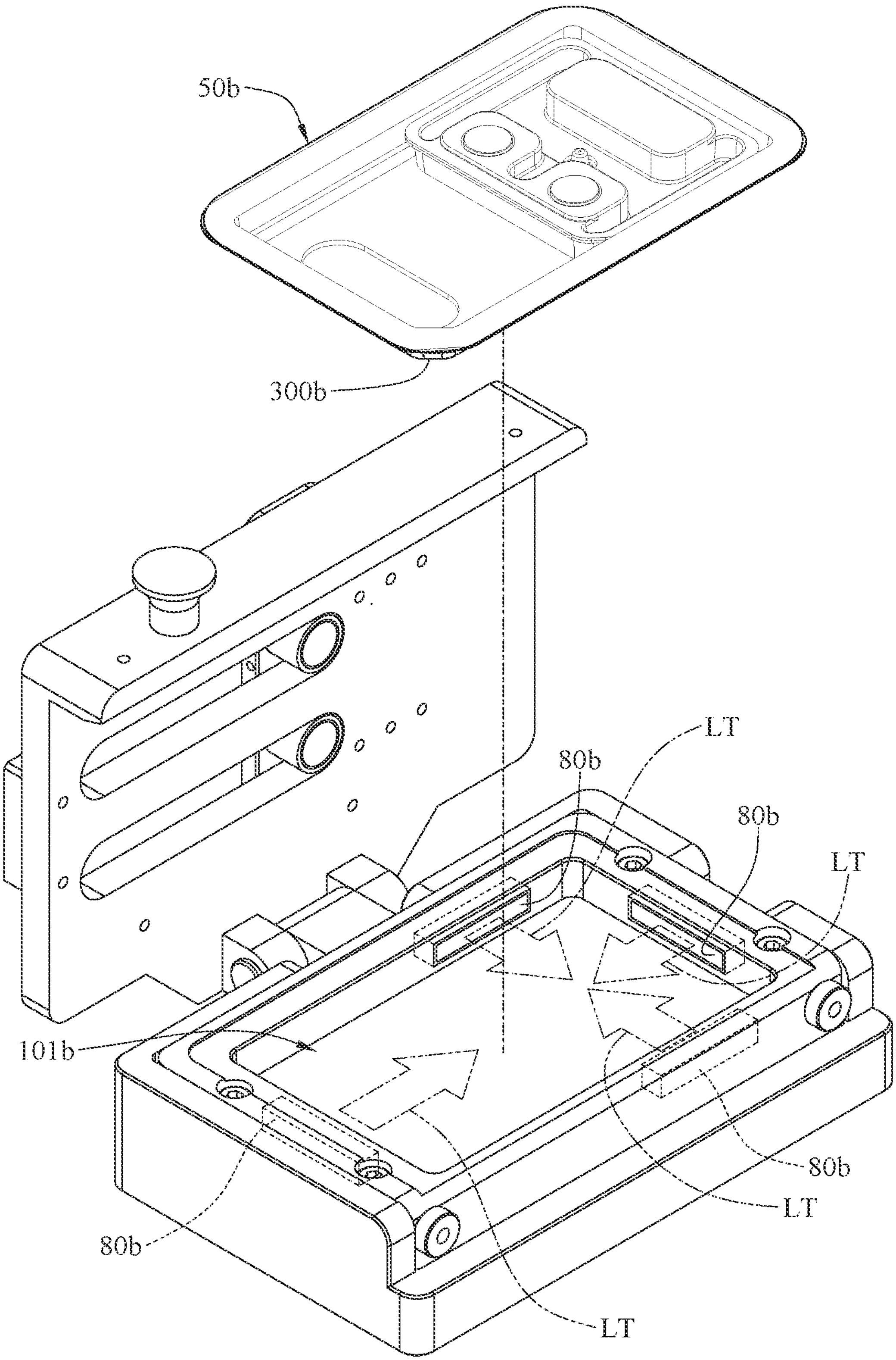
FIG. 14 is an exploded view of several parts of a biological tissue dispensing system according to further another embodiment of the present disclosure.

Please refer to FIG. 14, which is an exploded view of several parts of a biological tissue dispensing system according to further another embodiment of the present disclosure. Note that only differences between this and abovementioned embodiments will be illustrated hereinafter with the similar description omitted.

In this embodiment, the base 300*b* of the biological tissue forming package 50*b* is light-transmitting. There are four light sources 80*b* attached to the periphery of the accommodation space 101*b*. The light sources 80*b* provide curing light LT travelling into the biological tissue forming package 50*b* through the base 300*b* from the surrounding of the biological tissue forming package 50*b* for irradiating the biological tissue fluid therein, and the biological tissue fluid irradiated from the surrounding can also be cured. Please be noted that the quantity of the light source 80*b* is not intended to restrict the present disclosure.

Figure 15:
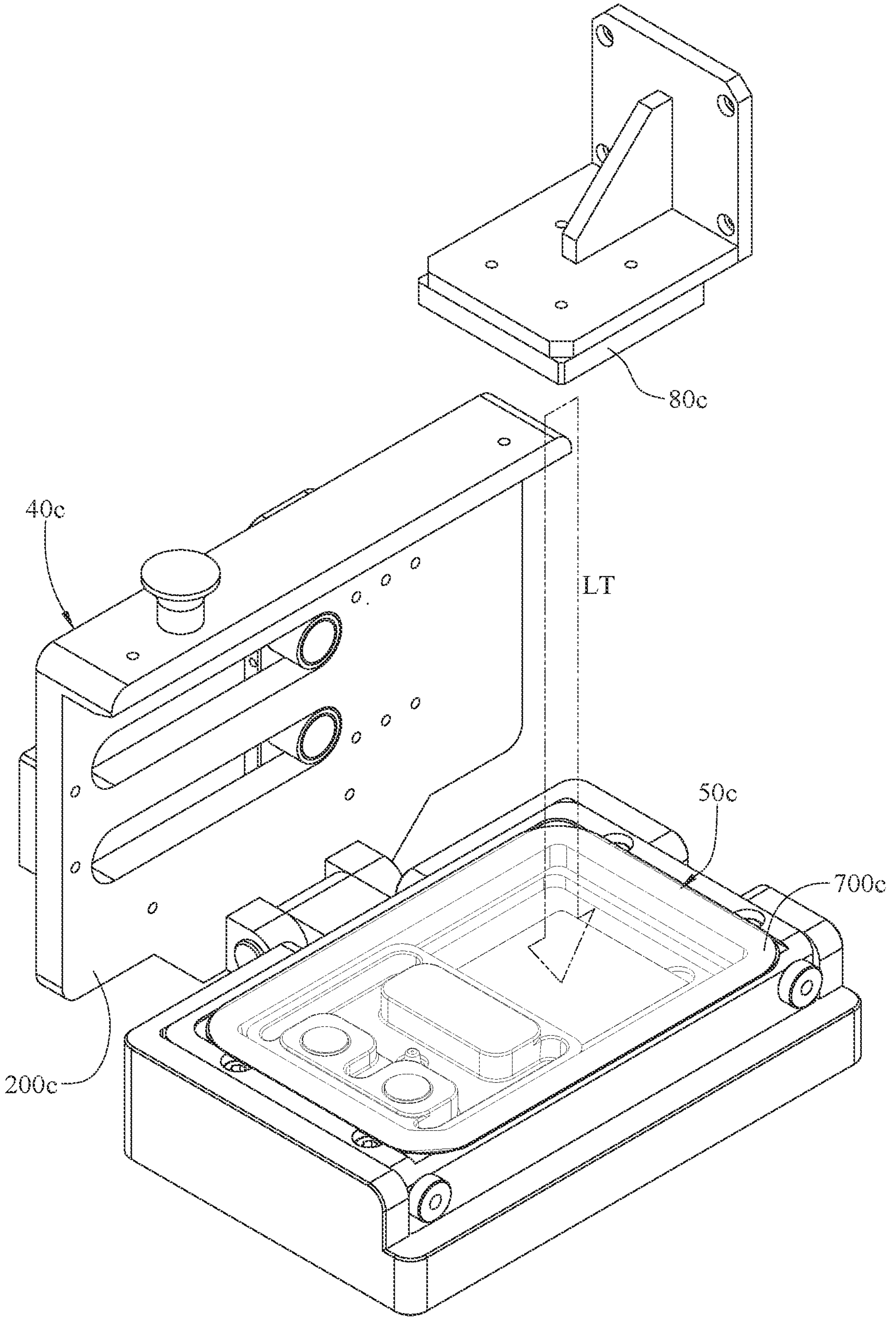
FIG. 15 is an exploded view of several parts of a biological tissue dispensing system according to still further another embodiment of the present disclosure.

Please refer to FIG. 15, which is an exploded view of several parts of a biological tissue dispensing system according to still further another embodiment of the present disclosure. Note that only differences between this and abovementioned embodiments will be illustrated hereinafter with the similar description omitted.

In this embodiment, the light source 80*c* is placed outside the carrier 40. The light source 80*c* can provide curing light LT travelling into the biological tissue forming package 50*c* through the sealing film 700*c* from the top of the biological tissue forming package 50*c* with the lid 200*c* opened for irradiating the biological tissue fluid therein, and the biological tissue fluid irradiated from the top can also be cured.

According to the biological tissue forming method, the biological tissue forming package and the biological tissue dispensing system discussed above, the present disclosure can provide a stable environment for quickly curing the biological tissue fluid, compared to the biological tissue fluid cured by heating in the conventional manner. Therefore, the biological tissue can be instantly produced for immediate usage after appropriate cells are collected from the cell bank. There is no need to provide a particular environment to transport or preserve the cured biological tissue for future usage, which can reduce the transportation and preservation cost of the biological tissue, and any risk such as contamination or damage to the biological tissue will be minimized during transportation or preservation.

Moreover, the heating used for curing biological tissue in the conventional manner may damage cells due to improper temperature control. In comparison, using the light source to irradiate the biological tissue fluid provides a stable forming environment.

Furthermore, with the design of the first recess, the cured biological tissue can be easily taken out with the membrane, preventing damage of the biological tissue caused by high temperature of laser cutting used for facilitating the acquisition of cured biological tissue in the conventional manner.

Additionally, since the biological tissue fluid is cured after being smoothened through the flat surface of the sliding assembly, the exposed surface of the cured and formed biological tissue is flat and thus can be adapted to different kinds of wounds.

Also, since the chamber sealed in the biological tissue forming package is sterilized without biological ingredient therein before dispensing the biological tissue fluid, the biological tissue forming package can be low-costly mass-produced and then can be easily and low-costly transported to and preserved at various medical facilities for future usage.

In addition, the sliding assembly can be moved in a contactless manner via the active magnetic elements, for maintaining the sterility of the chamber before dispensing the biological tissue fluid therein.

Please be noted that the signal communication mentioned in the present disclosure refers to a connection manner that signals can be transmitted between two components by, for example, a wired or wireless manner.

The embodiments are chosen and described in order to best explain the principles of the present disclosure and its practical applications, to thereby enable others skilled in the art best utilize the present disclosure and various embodiments with various modifications as are suited to the particular use being contemplated. It is intended that the scope of the present disclosure is defined by the following claims and their equivalents.

What is claimed is:

1. A biological tissue forming method, comprising:

providing a biological tissue forming package, wherein the biological tissue forming package comprises a base, a membrane, a sliding assembly and a sealing film, the base has a chamber for receiving the membrane and the sliding assembly, the sliding assembly is located at a covering position to cover the membrane, the sealing film seals the chamber, and one of the base and the sealing film is light-transmitting;

passing a biological tissue fluid through the sealing film and the sliding assembly so as to be dispensed on the membrane;

moving the sliding assembly away from the covering position via at least one passive magnetic element so as to expose the biological tissue fluid on the membrane; and irradiating the biological tissue fluid exposed on the membrane by a curing light transmitting through the one of the base and the sealing film so as to cure the biological tissue fluid into a biological tissue.

2. The biological tissue forming method according to claim 1, wherein the curing light irradiates the biological tissue fluid within a predetermined period of time.

3. The biological tissue forming method according to claim 1, after irradiating the biological tissue fluid to cure the biological tissue fluid, further comprising:

removing the sealing film to acquire the cured biological tissue.

4. The biological tissue forming method according to claim 1, wherein moving the sliding assembly to expose the biological tissue fluid is performed before irradiating the biological tissue fluid to cure the biological tissue fluid.

5. A biological tissue forming package, comprising:

a base, having a chamber and a supporting surface located in the chamber;

a membrane, made of a hydrophilic material, wherein the membrane is disposed on the supporting surface of the base;

a sliding assembly, movably disposed in the chamber of the base between a covering position and an exposing position; when the sliding assembly is located at the covering position, the sliding assembly correspondingly covers the membrane; when the sliding assembly is located at the exposing position, the sliding assembly is located away from and exposes the membrane;

at least one passive magnetic element, attached to the sliding assembly, wherein the at least one passive magnetic element is configured to be magnetically attracted to move the sliding assembly; and a sealing film, disposed on and covering the base to seal the chamber as well as the membrane, the sliding assembly and the at least one passive magnetic element inside the chamber;

wherein one of the base and the sealing film is light-transmitting; when the sliding assembly is located at the covering position, the sealing film and the sliding assembly are configured for a biological tissue fluid to pass therethrough so as to dispense the biological tissue fluid on the membrane; when the sliding assembly is located at the exposing position, the one of the base and the sealing film is configured for a curing light to transmit therethrough so as to irradiate the biological tissue fluid exposed on the membrane and cure the biological tissue fluid into a biological tissue.

6. The biological tissue forming package according to claim 5, wherein the sliding assembly has a flat surface facing towards the supporting surface so as to smoothen a surface of the biological tissue fluid during movement of the sliding assembly from the covering position to the exposing position.

7. The biological tissue forming package according to claim 5, wherein the sliding assembly has a first protrusion, and the first protrusion and the at least one passive magnetic element are spaced apart from and disposed opposite to each other along a movement direction of the sliding assembly.

8. The biological tissue forming package according to claim 5, wherein the sliding assembly comprises:

a first component, having a flat surface and a positioning element respectively located at two opposite sides thereof, wherein the flat surface faces towards the supporting surface, and the positioning element is a cylindrical protrusion; and a second component, disposed on the first component, wherein the second component has a first protrusion, a second protrusion and an opening, the first protrusion and the second protrusion are spaced apart from and disposed opposite to each other along a movement direction of the sliding assembly, the second protrusion has at least one recess for receiving the at least one passive magnetic element, and the opening is located between the first protrusion and the second protrusion and configured for the positioning element to pass therethrough.

9. The biological tissue forming package according to claim 5, wherein the supporting surface is recessed from a plate of the base so as to form a first recess, the base further has a second recess that is in communication with the chamber and the first recess for convenience of placement or removal of the membrane.

10. A biological tissue dispensing system, adapted for the biological tissue forming package of claim 5, the biological tissue dispensing system comprising:

a carrier, comprising:

a carrier body, having an accommodation space that is configured to accommodate the biological tissue forming package; and a lid, coupled to the carrier body for selectively opening or closing the accommodation space, wherein the lid has a dispensing hole in communication with the accommodation space;

at least one active magnetic element, movably attached to the lid; when the lid closes the accommodation space, the at least one active magnetic element is configured to magnetically attract the at least one passive magnetic element of the biological tissue forming package so as to move the sliding assembly between the covering position and the exposing position; and a dispenser, movably mounted with respect to the carrier, wherein the dispenser is configured to receive the biological tissue fluid therein; when the lid closes the accommodation space, one end of the dispenser is configured to move and pass through the dispensing hole, the sealing film and the sliding assembly so as to dispense the biological tissue fluid on the membrane.

11. The biological tissue dispensing system according to claim 10, further comprising a light source, wherein the sealing film is light-transmitting, the light source is attached to the lid, and the light source is configured to provide the curing light that passes through the sealing film and irradiates the biological tissue fluid exposed on the membrane so as to cure the biological tissue fluid into the biological tissue.

12. The biological tissue dispensing system according to claim 10, further comprising a light source, wherein the base is light-transmitting, the light source is attached to the carrier body, the light source is configured to provide the curing light that passes through the base and irradiates the biological tissue fluid exposed on the membrane so as to cure the biological tissue fluid into the biological tissue.

13. The biological tissue dispensing system according to claim 10, further comprising a forming machine and a light source, wherein the forming machine receives the carrier, the biological tissue forming package, the at least one active magnetic element and the dispenser therein to be isolated from external light, the light source is attached to the forming machine, the light source is configured to provide the curing light that irradiates the biological tissue fluid exposed on the membrane so as to cure the biological tissue fluid into the biological tissue.

* * * * *